United States Patent [19]
Moloney et al.

[11] Patent Number: 5,972,320
[45] Date of Patent: Oct. 26, 1999

[54] ANTIPERSPIRANT OR DEODORANT COMPOSITION WITH SILICONE LATEX

[75] Inventors: Michael J. Moloney, Brimfield; Michael W. Barry, Boston; Lorraine C. M. Blanchard, Newbury; Carl F. Iovanni, Cambridge, all of Mass.

[73] Assignee: The Gillette Company, Boston, Mass.

[21] Appl. No.: 08/898,294

[22] Filed: Jul. 21, 1997

Related U.S. Application Data

[63] Continuation-in-part of application No. 08/687,872, Jul. 26, 1996.

[51] Int. Cl.$^6$ .............................. A61K 7/32; A61K 31/74; A61K 7/00
[52] U.S. Cl. ..................... 424/65; 424/78.02; 424/78.03; 424/780.08; 424/400; 424/401
[58] Field of Search ................... 424/65, 78.02, 424/78.03, 78.08, 400, 401

[56] References Cited

U.S. PATENT DOCUMENTS

| | | | |
|---|---|---|---|
| 5,069,897 | 12/1991 | Orr | 424/66 |
| 5,628,989 | 5/1997 | Harashima et al. | 424/65 |
| 5,665,804 | 9/1997 | Hill et al. | 524/268 |
| 5,744,130 | 4/1998 | Guskey et al. | 424/65 |

FOREIGN PATENT DOCUMENTS

| | | |
|---|---|---|
| WO 97/44010 | 11/1997 | WIPO . |
| WO 98/00097 | 1/1998 | WIPO . |
| WO 98/00104 | 1/1998 | WIPO . |
| WO 98/00105 | 1/1998 | WIPO . |

*Primary Examiner*—Shelley A. Dodson
*Attorney, Agent, or Firm*—Stephan P. Williams

[57] ABSTRACT

The present invention is directed to a composition comprising an antiperspirant salt suspended in a carrier vehicle thickened with a silicone latex. The composition typically comprises about 50 to 90% carrier vehicle, which is advantageously substantially comprised of a volatile silicone, about 3 to 30% antiperspirant salt, which is typically an aluminum chlorohydrate or aluminum-zirconium chlorohydrate, and about 3–25% silicone latex. Preferably the composition will contain an auxiliary thickening agent such as a fumed silica, hydrated silica or trihydroxystearin, typically in an amount of 0.01 to 10%. The composition will preferably have a viscosity of about 12,000 to 20,000,000 cP. The present invention also embraces an apparatus for delivering the above-described composition when formulated with a medium viscosity of about 12,000 to 50,000 cP, said apparatus having a porous dome with a porosity of about 150 μm to 400 μm through which the composition is delivered.

24 Claims, 1 Drawing Sheet

ANTIPERSPIRANT OR DEODORANT COMPOSITION WITH SILICONE LATEX

CROSS-REFERENCE TO RELATED APPLICATIONS

This application is a continuation-in-part of application Ser. No. 08/687,872 filed on Jul. 26, 1996.

BACKGROUND OF THE INVENTION

This invention relates to antiperspirant and deodorant compositions which contain a silicone latex as a thickening agent. In particular it relates to such compositions which additionally contain an auxiliary thickening agent.

Silicone latex thickened solvents and cosmetic compositions containing such silicone latex thickened solvents are described in U.S. Ser. No. 08/596,853 filed on Feb. 5, 1996 now U.S. Pat. No. 5,665,804. The silicone latex is a high internal phase dispersion of crosslinked silicone rubber particles in water. When added to a solvent such as cyclomethicone, it swells and substantially increases the viscosity of the solvent. Antiperspirant compositions containing a silicone rubber powder are disclosed in U.S. Pat. No. 5,628,989.

SUMMARY OF THE INVENTION

The present invention is directed to a composition comprising an antiperspirant salt suspended in a carrier vehicle thickened with a silicone latex. The composition typically comprises about 50 to 90% carrier vehicle, which is advantageously substantially comprised of a volatile silicone, about 3 to 30% antiperspirant salt, which is typically an aluminum chlorohydrate or aluminum-zirconium chlorohydrate, and about 3–25% silicone latex. Preferably the composition will contain an auxiliary thickening agent such as a fumed silica, hydrated silica or trihydroxystearin, typically in an amount of about 0.01 to 10%. The composition will preferably have a viscosity of about 12,000 to 50,000 cP (medium viscosity embodiment). Compositions having a creamy to soft solid texture (i.e. a viscosity of 80,000 to 20,000,000 cP (high viscosity embodiment)) may also be prepared by adjusting the amount of silicone latex thickener and auxiliary thickening agent. The present invention also embraces an apparatus for delivering the above-described medium viscosity composition, said apparatus having a porous dome with a porosity of about 150 $\mu$ to 400 $\mu$ through which the composition is delivered.

DETAILED DESCRIPTION OF THE INVENTION

Figure 1:
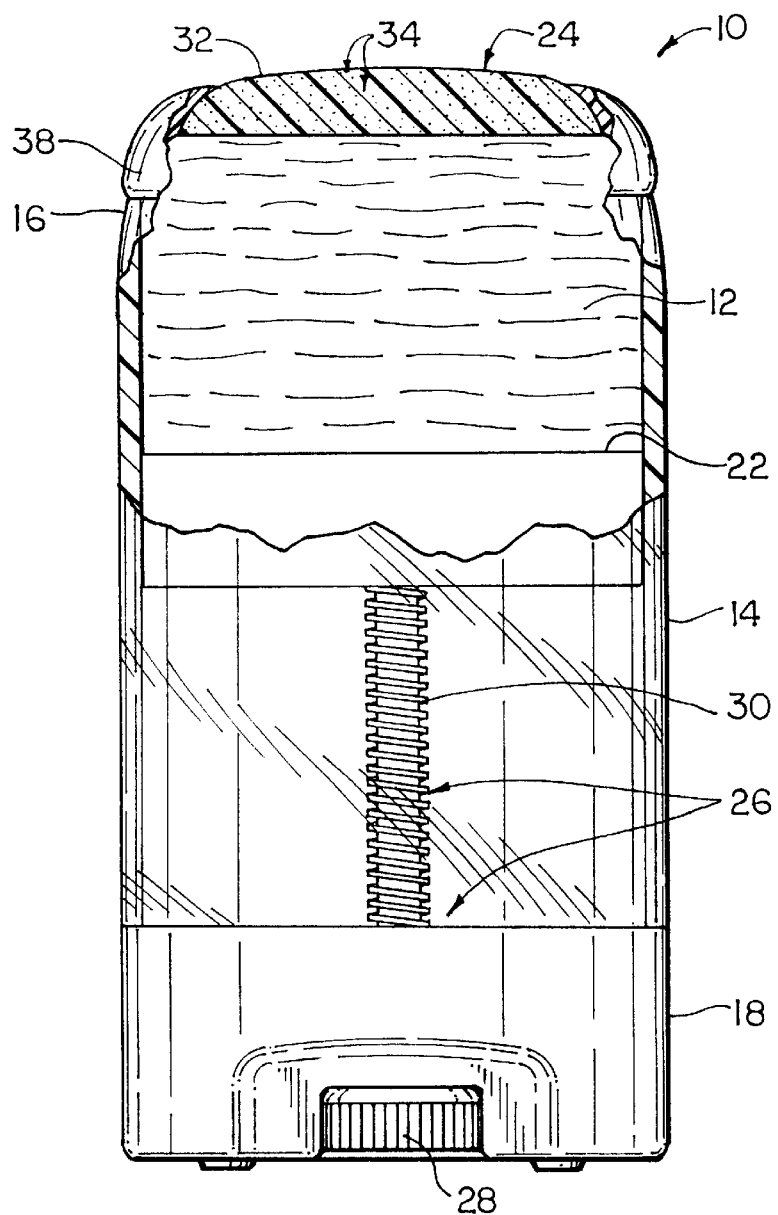
FIG. 1 is a front elevational view, shown in partial cross section, of a dispenser for a medium viscosity antiperspirant or deodorant composition of the present invention.

The antiperspirant and deodorant compositions of the present invention will include as the main vehicle a silicone latex thickened organic and/or silicone compound.

The silicone latex is a high solids dispersion of crosslinked silicone rubber particles in water. The silicone latex is described in U.S. Ser. No. 08/596,853 filed on Feb. 5, 1996 now U.S. Pat. No. 5,665,804 (see also EP 739,947 and EP 739,928), the contents of which are incorporated herein by reference. The silicone latex is the hydrosilation reaction product of a vinyl functional siloxane polymer and a hydride functional siloxane polymer prepared in an aqueous emulsion. The vinyl functional siloxane polymer is represented by the formula $CH_2=CH-((CH_3)_2SiO)_x-(CH_3)_2Si-CH=CH_2$ in which x is an integer such that the viscosity of the polymer is between 5000 and 60,000 cP. The hydride functional siloxane polymer is represented by the formula $(CH_3)_3SiO((CH_3)_2SiO)_y(CH_3HSiO)_zSi(CH_3)_3$ in which y is an integer between 3 and 20 and z is an integer greater than 3 and less than 10. The silicone latex is formed by emulsifying 100 parts of siloxane polymer with 0.5 to 10 parts surfactant, such as Isolaureth-6 or PPG-3-Deceth-3, and 0.5 to 25 parts water, adding catalyst and crosslinker or self-catalytic crosslinker, and curing to form a dispersion of the silicone rubber particles in water. Preferably the silicone latex has a high solids content of at least 90% crosslinked silicone rubber particles.

A preferred silicone latex is prepared by emulsifying 89.5 parts of a vinyl endblocked silicone polymer (55,000 cst, 0.88% vinyl, 30810 eq. wt. vinyl, degree of polymerization=830), 0.4 parts of a dimethyl, methylhydrogen siloxane $[(CH_3)_3SiO((CH_3)_2SiO)_8(CH_3HSiO)_4Si(CH_3)_3]$, with 2.7 parts of a 45% aqueous solution of polyoxyethylene (3), polyoxypropylene (3) decyl ether (PPG-3-Deceth-3). The emulsified silicone is then diluted to 90% solids using 7.1 parts water and the silicone phase and particles are crosslinked by adding 0.2 parts of a platinum complex. A preservative (i.e. microbiocidal agent) is preferably added to the silicone latex.

For easier use and handling the silicone latex is blended with cyclomethicone, preferably octamethylcyclotetrasiloxane (D4) or decamethylcyclopentasiloxane (D5) or a mixture thereof. The silicone latex/cyclomethicone blend will typically comprise about 5–40%, preferably 5–15%, more preferably 10–12% silicone latex in about 60–95%, preferably 85–95%, more preferably 88–90% cyclomethicone with about 0.001–10%, preferably 0.01–1%, more preferably 0.05–0.4% of a water-in-cyclomethicone stabilizing surfactant such as an ethoxylated, propoxylated siloxane (e.g. dimethicone copolyol). A preferred blend comprises 11 parts of the aforedescribed silicone latex, 88.9 parts cyclomethicone and 0.1 parts dimethicone copolyol. The silicone latex blend will also preferably contain a preservative. Preferred silicone latex/cyclomethicone blends are available from Dow Corning as DC-2-9060 and DC-2-9065 (possible INCI name is Cyclomethicone and Dimethicone/Vinyl Dimethicone Crosspolymer and PPG-3-Deceth-3 and Dimethicone Copolyol). When used in this form, the blend should be added in an amount which gives the desired quantity of silicone latex in the final composition.

The amount of silicone latex to be incorporated into the composition may be varied depending upon the thickening or viscosity desired in the final composition, which may range from a thick liquid to a cream or gel consistency up to a paste or soft-solid. Generally, the silicone latex will be utilized in an amount of about 3 to 25% by weight of the composition, preferably about 5 to 20%. Most preferably, the amount of silicone latex will comprise about 6 to 12% by weight of the composition.

The main portion of the carrier vehicle will be an organic or silicone compound or mixtures thereof. Preferably, the vehicle will be comprised substantially of a volatile silicone. Volatile silicones are well-known in the art and may be linear or cyclic. They have a boiling point under 250° C. and a viscosity less than 10 cP. Preferred are the cyclomethicones such as DC 244, DC 245, DC 344 and DC 345. The volatile silicones give the composition a dry feel and leave substantially no residue.

While volatile silicones are preferred, other silicones and/or organic compounds may be utilized in the carrier vehicle, particularly when included in addition to the volatile silicones to improve application aesthetics. These include non-volatile silicones such as dimethicone and dimethicone copolyol and aliphatic hydrocarbons such as mineral oil and hydrogenated polyisobutene. Of course, a variety of well-known emollients such as diisopropyl adipate, diisopropyl sebacate, PPG-5-Ceteth-20, Octyl Isononanoate, and PPG-14 Butyl Ether may be included in the vehicle to improve application aesthetics. Generally, the vehicle will comprise about 50 to 90% of the composition by weight, preferably about 65 to 85%.

Antiperspirant salts which may be used in the compositions of the present invention include any of the conventional aluminum, zirconium and aluminum-zirconium salts known to be useful in antiperspirant compositions. These salts include aluminum halides and aluminum hydroxy halides (e.g., aluminum chlorohydrate), and mixtures or complexes thereof with zirconyl oxyhalides and zirconyl hydroxyhalides (e.g. aluminum-zirconium chlorohydrate). It has been surprisingly found that addition of the antiperspirant salt to a silicone latex thickened carrier vehicle substantially further increases the viscosity of the composition, thus making it possible to readily achieve a more viscous composition, especially one with a creamy type consistency.

Preferred aluminum salts are those having the general formula $Al_2(OH)_{6-a}X_a$ wherein X is Cl, Br, I or $NO_3$, and a is about 0.3 to about 4, preferably about 1 to 2, such that the Al to X mole ratio is about 1:1 to 2.1:1. These salts generally have some water of hydration associated with them, typically on the order of 1 to 6 moles per mole of salt. Most preferably, the aluminum salt is aluminum chlorohydrate (i.e. X is Cl) and a is about 1, such that the aluminum to chlorine mole ratio is about 1.9:1 to 2.1:1.

Preferred aluminum-zirconium salts are mixtures or complexes of the above-described aluminum salts with zirconium salts of the formula $ZrO(OH)_{2-pb}Y_b$ wherein Y is Cl, Br, I, $NO_3$, or $SO_4$, b is about 0.8 to 2, and p is the valence of Y. The zirconium salts also generally have some water of hydration associated with them, typically on the order of 1 to 7-moles per mole of salt. Preferably the zirconium salt is zirconyl hydroxychloride of the formula $ZrO(OH)_{2-b}Cl_b$ wherein b is about 1 to 2, preferably about 1.2 to about 1.9. The preferred aluminum-zirconium salts have an Al:Zr ratio of about 1.7 to about 12.5, most preferably about 2 to about 10, and a metal:X+Y ratio of about 0.73 to about 2.1, preferably about 0.9 to 1.5. A preferred salt is aluminum-zirconium chlorohydrate (i.e. X and Y are Cl), which has an Al:Zr ratio of about 2 to about 10 and a metal:Cl ratio of about 0.9 to about 2.1. Thus, the term aluminum-zirconium chlorohydrate is intended to include the tri-, tetra-, penta- and octa-chlorohydrate forms. The aluminum-zirconium salt complexes may also contain a neutral amino acid, preferably glycine, typically with a Gly:Zr ratio of about 1:1 to 4:1.

It is especially preferred to utilize enhanced efficacy aluminum and aluminum-zirconium antiperspirant salts in the compositions of the present invention. By "enhanced efficacy antiperspirant salts" is meant antiperspirant salts which, when reconstituted as 10% aqueous solutions, produce an HPLC chromatogram (as described, for example, in U.S. Pat. No. 5,330,751, which is incorporated herein by reference) wherein at least 70%, preferably at least 80%, of the aluminum is contained in two successive peaks, conveniently labeled peaks 3 and 4, wherein the ratio of the area under peak 4 to the area under peak 3 is at least 0.5, preferably at least 0.7, and most preferably at least 0.9 or higher. Any suitable HPLC technique may be employed provided that it is capable of resolving the Al component into five peaks. The enhanced efficacy (or activated) antiperspirant salts are well-known in the industry and are commercially available from several suppliers.

Sufficient antiperspirant salt should be added so that the final composition, after all components are added, includes between about 3% and about 30%, preferably about 6% to 25%, of the antiperspirant salt by weight. Generally, the composition will be designated an antiperspirant composition if it contains sufficient antiperspirant salt to effectively inhibit perspiration. This amount of antiperspirant salt will typically be greater than about 10% by weight. Below that amount, the composition will generally be designated a deodorant composition. It should be noted that reference throughout this application to weight percent of antiperspirant salt is intended to be calculated in accordance with the standard industry method, which includes bound water and glycine. If the amount of antiperspirant salt is calculated in accordance with the new U.S.P. method, which excludes bound water and glycine, the range of weight percent will be somewhat lower. It is especially preferred to utilize a particulate antiperspirant salt with a relatively small particle size, preferably in the range of about 1 to 50 $\mu$m, to achieve the best suspension and aesthetic characteristics. Most preferred are ultrafine antiperspirant salts wherein at least 90% of the particles are under 11 $\mu$m.

While the compositions of the present invention may be formulated and used with only the above-described basic constituents, it is also desirable to add other optional components to achieve desired application aesthetics or other effects. For example, the addition of auxiliary thickening agents has been found to substantially improve the application aesthetics by thickening or increasing the viscosity of the composition to desired levels while maintaining the amount of the silicone latex at relatively low levels. It has been found that high levels of the silicone latex, while effective at thickening the composition, tend to diminish the application aesthetics, for example by giving a too greasy and/or too sticky feel. The addition of an auxiliary thickening agent, especially the preferred silicas, give the composition a drier, less sticky feel.

Any conventional thickening agents known for use in antiperspirant and deodorant compositions may be utilized, alone or in combination, as an auxiliary thickening agent in the compositions of the present invention. These include waxes, fatty acids, fatty alcohols, fatty amides, clays, silicas, starches, silicate powders, particulate polyolefins (e.g. polyethylene), etc. Especially useful thickening agents include fumed silicas, precipitated silicas, hydrated silicas (e.g. Sylox 2 from Grace Davison, Sipernat 22S from Degussa), trihydroxystearin (glyceryl tri (12-hydroxystearate) (Thixin R)), tribehenin (glyceryl tribehenate (Synchrowax HR-C)), calcium aluminum borosilicate (Presperse from Luxsil) and silicone gum (e.g. DC-1401). The auxiliary thickening agent may be added in an amount of about 0.01 to 10%, preferably about 0.1 to 5%, by weight of the composition, depending upon the desired viscosity of the product. Mixtures of two or more of such auxiliary thickening agents may be included in the composition.

Particularly advantageous as auxiliary thickening agents are the silicas, preferably fumed silicas, which have been found to substantially increase the viscosity of the composition at very low levels. Generally, the silica will be added in an amount of less than 1%, preferably less that 0.5%, and more preferably less than 0.1% (e.g. 0.01 to 0.1% for medium viscosity compositions). Obviously, higher amounts of silica will be used for the high viscosity compositions and lower amounts for the medium viscosity compositions. It has been surprisingly found that an amount as low as 0.01% to 0.02% fumed silica will substantially increase the viscosity of the composition, particularly when the composition contains higher levels (i.e. >12%) of antiperspirant salt. Especially preferred silicas are Aerosil 200 and Aerosil 300, available from Degussa Corporation.

Also advantageous as auxiliary thickening agents are the hydrated silicas such as Sylox 2, available from Grace Davison, and Sipernat 22S, available from Degussa. The hydrated silicas provide the composition with especially desirable aesthetic attributes, particularly when used in an amount of about 0.1 to 5%, preferably about 0.5 to 2%, by weight. Other desirable thickening agents include trihydroxystearin, typically in amounts of about 0.1 to 3%, preferably 0.2 to 1.5%, and calcium aluminum borosilicate, typically in amounts of about 0.5 to 5%, preferably about 1 to 3%. Obviously, the selection of auxiliary thickening agent or mixture of such agents and the amount thereof may be varied to achieve a desired viscosity or firmness in the final composition, as well as a desired aesthetic attribute.

The composition may contain an antimicrobial or deodorant active agent such as triclosan or hyamine. These agents are typically included in an amount of about 0.1 to about 3% by weight of the composition. The composition may also contain a fragrance oil or encapsulated fragrance powder, which is typically included in an amount of less than 2.5%, preferably less than about 1.5%, of the composition by weight.

The viscosity of the composition may be adjusted to any desired level (e.g. between about 12,000 to 20,000,000 cP) by adjusting the amount of silicone latex along with any auxiliary thickening agent or agents present. It has been found that a composition with especially desirable application aesthetics will have a medium viscosity of about 12,000 to 50,000 cP, preferably about 18,000 to 30,000 cP. It has been found that such a composition may advantageously be delivered through an applicator with a porous dome having an average pore size of about 150 to 400 $\mu$m, preferably about 250 $\mu$m. Such a porous dome is made from polyolefin particles such as low density polyethylene particles (preferably spherical particles) which have been sintered or fused together into a dome shape. Such porous domes are available from Porex Technologies and Interflo Technologies.

While porous domes have been previously used to deliver liquid compositions (see, for example U.S. Pat. Nos. 4,050,826 and 5,230,579), it is not believed that anyone considered it possible or desirable to deliver a viscous or cream-like composition through such a dome. This may be due to the fact that the domes previously used had a much lower porosity and could not effectively deliver a viscous or cream-like composition as contemplated by the present invention. However, the combination of a composition with a medium viscosity of 12,000 to 50,000 cP, preferably 18,000 to 30,000 cP, with a porous dome of 150 to 400 $\mu$m, preferably about 250 $\mu$m, porosity has been found to provide excellent application aesthetics and is considered highly desirable to the consumer.

Compositions of the present invention having a higher viscosity or stiffness, typically characterized as a cream up to a soft solid, are also highly desirable. These compositions will typically have a viscosity of about 50,000 to 20,000,000 cP, preferably about 80,000 to 20,000,000 cP, more preferably about 100,000 to 10,000,000 cP at 1 sec$^{-1}$. These compositions may also be described by reference to penetration force value. The antiperspirant soft solid creams described in the higher viscosity range have penetration force values from about 150 to 800 g, preferably from about 200 to 600 g, and most preferably from about 250 to 500 g as measured with a TA.XT2 Texture Analyzer, manufactured by Texture Technologies Corp. These penetration force values are a measure of the force required to move a 2.0 cm diameter disk a distance of 15.0 mm through the product at a rate of 2.0 mm/sec.

Figure 2:
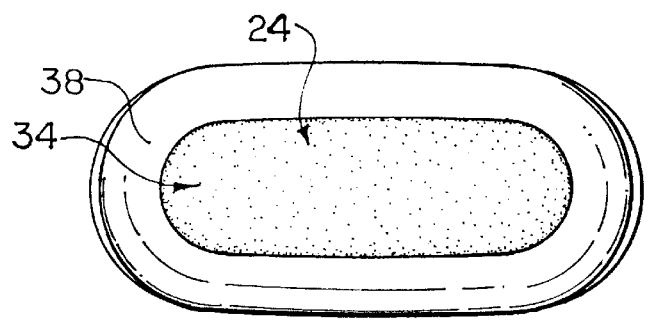
FIG. 2 is a top plan view of the dispenser of FIG. 1, which illustrates the porous dome through which the antiperspirant or deodorant composition is dispensed.

Referring now to FIGS. 1 and 2, there is illustrated an apparatus 10 for dispensing a cream or thin paste 12 having a viscosity of 12,000 to 50,000 cP, preferably 18,000 to 30,000 cP, the apparatus being comprised of a container 14 having a top end 16 and a bottom end 18 and a container opening being defined between the top end and the bottom end. The container 14 is filled with a cream or thin paste 12 within the container reservoir, which is that portion of the container opening between the platform 22 and the porous dome 24.

A transport mechanism 26 is operatively engaged to the bottom end 18 of the container, the transport mechanism capable of transporting the cream 12 toward the top end 16 of the container 14. The transport mechanism 26 will typically include a turn buckle 28 coupled to a threaded shaft 30 which threadedly engages the platform 22, as is well known to the art. Rotary motion of the turn buckle 28 causes the platform to advance upwardly on threaded shaft 30. This upward movement of the platform forces the cream 12 upwardly towards the porous dome 24.

The porous dome 24 is operatively engaged to the top end 16 of the container and is formed across at least a portion of the top end opening. The porous dome has a top end surface 32 formed on the upper surface of the porous dome 24. The porous dome 24 is made from a sintered low density polyethylene and has interconnected pores 34 defined therethrough which give it a porosity of about 150 to 400 $\mu$m, preferably about 250 $\mu$m. The porous dome 24 is operatively engaged to the container 14 such as by use of a support skirt 38 which is operatively engaged to the top end of the container 14.

In operation, the transport mechanism 26 forces the cream or thin paste 12 to flow from the container opening through the pores of the porous dome 24 to the top end surface 32. The porous dome is typically shaped to engage with portions of the human body such as the underarm and is, therefore, typically formed to have a smooth rounded contoured shape to ease application of the cream or thin paste to the skin.

The invention may be further described by the following examples.

EXAMPLES 1 to 5

Antiperspirant (medium viscosity)

| | Weight Percent | | | | |
|---|---|---|---|---|---|
| Ingredient | Ex. 1 | Ex. 2 | Ex. 3 | Ex. 4 | Ex. 5 |
| Silicone latex[1] | 6.00 | 6.00 | 6.00 | 6.30 | 6.30 |
| Cyclomethicone[2] | 70.35 | 68.85 | 68.94 | 68.64 | 68.34 |

-continued

| Ingredient | Ex. 1 | Ex. 2 | Ex. 3 | Ex. 4 | Ex. 5 |
|---|---|---|---|---|---|
| | | | Weight Percent | | |
| Al—Zr tetrachlorohydrate-gly | 23.50 | 23.50 | 23.50 | 23.50 | 23.50 |
| Dimethicone copolyol[3] | | | 0.75 | 0.75 | 0.75 |
| Diisopropyl adipate | | 1.00 | 0.60 | 0.60 | 0.60 |
| Silicone wax[4] | | 0.50 | | | |
| Silica[5] | | | 0.01 | 0.01 | 0.01 |
| Fragrance | 0.15 | 0.15 | 0.20 | 0.20 | 0.20 |

| Ingredient | Ex. 6 | Ex. 7 | Ex. 8 | Ex. 9 | Ex. 10 |
|---|---|---|---|---|---|
| | | | Weight Percent | | |
| Silicone latex[1] | 6.50 | 6.50 | 7.20 | 7.20 | 6.50 |
| Cyclomethicone[2] | 81.15 | 87.60 | 73.50 | 76.80 | 82.50 |
| Al—Zr tetrachlorohydrate-gly | 8.00 | 4.50 | 8.00 | 6.00 | 7.00 |
| Dimethicone copolyol[3] | | | | | 0.80 |
| Diisopropyl adipate | 3.00 | | 3.00 | 3.00 | 2.00 |
| Silica[5] | 0.35 | 0.35 | | | 0.20 |
| Fragrance | 1.00 | 0.75 | 1.00 | 1.00 | 1.00 |
| Triclosan | | 0.30 | 0.30 | 3.00 | |
| Zinc oxide | | | 7.00 | | |
| Al starch octenyl succinate[6] | | | | 3.00 | |

EXAMPLES 11 to 15

Antiperspirant (soft solid)

| Ingredient | Ex. 11 | Ex. 12 | Ex. 13 | Ex. 14 | Ex. 15 |
|---|---|---|---|---|---|
| | | | Weight Percent | | |
| Silicone latex[1] | 6.00 | 5.00 | 6.00 | 6.50 | 6.00 |
| Cyclomethicone[2] | 57.80 | 61.90 | 69.30 | 64.05 | 58.80 |
| Dimethicone[7] | 10.00 | 5.00 | | 5.00 | 10.00 |
| Al—Zr tetrachlorohydrate-gly | 23.50 | 23.50 | 23.50 | 23.50 | 23.50 |
| Trihydroxystearin[8] | 0.40 | | | 0.25 | 0.40 |
| Hydrated Silica[9] | 1.00 | 1.50 | 1.00 | 0.50 | |
| Silica[5] | | 0.30 | | | 0.10 |
| Calcium Aluminum Borosilicate | | 1.50 | | | |
| Fragrance | 1.30 | 1.30 | 0.20 | 0.20 | 1.20 |

[1] DC 2-9060 (Dow Corning). A blend of 11% silicone latex DC 3-2360 in cyclomethicone. The weight percent given represents the amount of silicone latex added.
[2] DC 344 (Dow Corning). A substantial portion is included with the DC 2-9060, the balance being added as DC 344. The weight percent is the total from both sources.
[3] Abil B-8851 (Goldschmidt) (EO/PO = 70/30)
[4] DC 2503 (Dow Corning)
[5] Aerosil 200 (Degussa)
[6] Dry-Flow Starch (National Starch)
[7] DC 225 (Dow Corning)
[8] Thixin R (Degussa)
[9] Sylox 2 (Grace Davison)

The above-described compositions were made in the following manner. All of the ingredients except for the Al—Zr salt, silica, fragrance, zinc oxide (if present) and starch (if present) are combined in a closed mixing vessel equipped with a dual 3-blade impeller and mixed until uniform. If Thixin R is present, it is added prior to the addition of silicone latex, then the mixture, after addition of the silicone latex, is heated to 50° C. and mixed under high shear agitation for twenty minutes. The silica (if present) is added, mixed until uniform, and the mixture is passed through a Sonolator shear device (Sonic Corp., Model A running at 500 psi through a 0.004 in. diameter orifice) to increase the viscosity, then flowed into another closed mixing vessel equipped with both a side scraping agitator and a central impeller. The Al-Zr salt is added and mixed until uniform, then the zinc oxide (if present) or starch (if present) is added. This addition further increases the viscosity. The fragrance is then added and mixed until uniform.

While particular embodiments of the invention have been shown and described for illustrative purposes, it will be apparent to those skilled in the art that various changes and modifications may be made without departing from the spirit and scope of the invention, which is defined by the claims which follow.

What is claimed is:

1. A composition comprising, by weight, about 3 to 30% of an antiperspirant salt suspended in about 50 to 90% of a carrier vehicle thickened with about 3 to 25% of a silicone latex and an auxiliary thickening agent.

2. The composition of claim 1 wherein the auxiliary thickening agent is selected from the group consisting of fumed silica, precipitated silica, hydrated silica, trihydroxystearin, tribehenin, calcium aluminum borosilicate and silicone gum.

3. The composition of claim 1 wherein the auxiliary thickening agent is a silica.

4. The composition of claim 1, 2 or 3 wherein the carrier vehicle comprises a volatile silicone.

5. The composition of claim 4 having a viscosity of about 12,000 to 50,000 cP.

6. The composition of claim 4 having a viscosity of about 50,000 to 20,000,000 cP.

7. The composition of claim 4 having a penetration force value of about 150 to 800 g.

8. The composition of claim 1 comprising about 65 to 85% carrier vehicle, about 6 to 25% antiperspirant salt and about 5–20% silicone latex.

9. The composition of claim 8 comprising about 6–12% silicone latex.

10. The composition of claim 8 wherein the carrier vehicle comprises a volatile silicone.

11. The composition of claim 10 wherein the auxiliary thickening agent is selected from the group consisting of fumed silica, precipitated silica, hydrated silica, trihydroxystearin, tribehenin, calcium aluminum borosilicate and silicone gum.

12. The composition of claim 10 wherein the auxiliary thickening agent comprises trihydroxystearin.

13. The composition of claim 10 wherein the auxiliary thickening agent comprises hydrated silica.

14. The composition of claim 10 wherein the auxiliary thickening agent comprises calcium aluminum borosilicate.

15. The composition of claim 10 wherein the auxiliary thickening agent comprises fumed silica.

16. The composition of claim 15 comprising 0.01 to 0.1% silica.

17. The composition of claim 1, 10 or 11 wherein the antiperspirant salt is aluminum chlorohydrate or aluminum-zirconium chlorohydrate.

18. The composition of claim 8 wherein the antiperspirant salt has a particle size distribution such that at least 90% of the particles are less than 11 $\mu$m.

19. The composition of claim 1, 10 or 11 wherein the silicone latex is the hydrosilation reaction product of a vinyl functional siloxane polymer and a hydride functional siloxane polymer prepared in aqueous emulsion, wherein the vinyl functional siloxane polymer is represented by the formula $CH_2=CH-((CH_3)_2SiO)_x-(CH_3)_2Si-CH=CH_2$ in which x is an integer such that the viscosity of the polymer is between 5000 and 60,000 cP, and wherein the hydride functional siloxane polymer is represented by the formula $(CH_3)_3SiO((CH_3)_2SiO)_y(CH_3HSiO)_zSi(CH_3)_3$ in which y is an integer between 3 and 20 and z is an integer greater than 3 and less than 10.

20. The composition of claim 10 or 11 having a viscosity of about 12,000 to 50,000 cP.

21. The composition of claim 10 or 11 having a viscosity of about 50,000 to 20,000,000 cP.

22. The composition of claim 10 or 11 having a penetration force value of about 150 to 800 g.

23. A method of inhibiting perspiration and/or preventing malodor in the axilla comprising applying to the axilla a composition according to claim 1, 10 or 11.

24. A method of inhibiting perspiration and/or preventing malodor in the axilla comprising applying to the axilla a composition according to claim 22.

* * * * *